United States Patent [19]
Raveh

[11] Patent Number: 5,807,396
[45] Date of Patent: Sep. 15, 1998

[54] BONE PLATE WITH CONICAL HOLES

[75] Inventor: Joram Raveh, Liebefeld-Bern, Switzerland

[73] Assignee: Howmedica Leibinger GmbH, Freiburg, Germany

[21] Appl. No.: 768,831

[22] Filed: Dec. 18, 1996

[30]  Foreign Application Priority Data

Dec. 22, 1995 [DE] Germany .................. 195 48 395.2

[51] Int. Cl.$^6$ ............................................. A61B 17/80
[52] U.S. Cl. ........................................ 606/69; 606/73
[58] Field of Search ........................... 606/69, 70, 71, 606/72, 73, 61, 60

[56]  References Cited

FOREIGN PATENT DOCUMENTS

| | | |
|---|---|---|
| 0048038A1 | 3/1982 | European Pat. Off. . |
| 0201024A1 | 11/1986 | European Pat. Off. . |
| 675531A5 | 10/1990 | Switzerland . |

*Primary Examiner*—Guy V. Tucker
*Attorney, Agent, or Firm*—Peter C. Richardson; Lawrence C. Akers; Raymond W. Augustin

[57]  ABSTRACT

An osteosynthesis device comprises a plate and screws which are screwed into bone through holes in the plate. The diameters of the holes at the top face of the plate are larger than at the bottom face of the plate. The screws have a spherical head which, when screwed in rests snugly against the wall of the screw hole with an annular contact surface. Both when the screw is located perpendicularly with respect to the plate and when located at an angle with respect to the plate, the contact surface is located above the center line of the hole depth.

12 Claims, 3 Drawing Sheets

BONE PLATE WITH CONICAL HOLES

BACKGROUND of the INVENTION

1. Field Of The Invention

The invention relates to an osteosynthesis device comprising a bone plate with a top face and a bottom face. The bottom face is located opposite the top face and is directed towards a bone. The plate has a plurality of screw holes which are located along the plate. The diameter of the screw holes at the top face of the plate is larger than the diameter at the bottom plate face. Screws are provided which can be screwed into the bone through the screw holes and have an at least partially rounded head which, when screwed-in, contacts the inner wall of the screw hole.

2. Description of the Prior Art

An osteosynthesis device similar to the plate herein is shown in Swiss patent CH 675 531 A5. The osteosynthesis fixation device which is described in this document is intended to ensure rigid, functionally stable fixation (local positioning) between the head of the bone screw and the osteosynthesis plate. In the prior art of CH 675 531 A5, the line of contact between the spherical screw head and the conical screw hole is located approximately centrally between the bottom face and the top face of the osteosynthesis plate. The conical plate hole and the screw head are designed such that when the screws are angled and are tightened, the screw head may push its way through the plate. As a result, stable fixation of the screw head on the plate is not ensured.

SUMMARY OF THE INVENTION

The object of the present invention is to combine the advantages of known external fixing (external fixator) with the advantages of known internal plate fastening (internal fixator) in order to achieve anchorage of the implant which is functionally stable over a long period of time. The prior art largely achieves the above mentioned aims with the aid of expandable screw heads and thus avoids bone absorption at the bearing surface between the plate and the bone. However, with such a device, it is only possible for the screw to be introduced at right angles to the plate and inserted into the bone and not angled with respect to the bone (see for example U.S. Pat. 4,484,570).

The object of the invention is to improve the osteosynthesis device of CH 675 531 further as regards to the functional stability over a long period of time and to eliminate to the greatest possible extent the occurrence of loosening due to stressing and loading transmitted to the bone and plate during functional movement.

The present invention achieves this object in that, when the screw is located perpendicularly with respect to the plate, the contact surface is closer to the top face of the plate than to the bottom face thereof, which location is not taught in the prior art.

This new design principle achieves and ensures stable wedging and fixation of the screw head on the plate without an expandable screw head being necessary. The contact takes place above the center line of the plate hole and the situation where the screw head pushes its way through is thus avoided. Thus, stable annular fixation and wedging of the screw head over the entire plate-hole region being achieved even when the screw is set at an angle. This is accomplished by the relative diameter of the rounded screw head and the diameter and angulation of the conical hole in the bone plate.

Preferably, all points of the contact surface are closer to the top osteosynthesis-plate face, which is directed away from the bone, than to the bottom face of said plate. It has, surprisingly, turned out to be the case that this design achieves an improvement along the lines of the object outlined above. Furthermore, the positioning of the contact surface between screw head and screw hole taught herein secures the screw to an optimum extent against slipping through the hole when subjected to pronounced tensile stressing.

In contrast to the majority of such devices of the prior art, the osteosynthesis device according to the present invention permits firm internal fixing of bone fragments without the plate having to be matched directly to the bone. This avoids pronounced pressure being exerted on the bone surface as well as the associated risk of bone absorption and osteolysis. This is particularly significant for the fixation (local securing) of convex or concave bone fragments in which there is no contact, or only very little contact, with the bottom face of the plate.

The invention ensures that the screw head is fixed in the hole of the osteosynthesis plate rigidly and so as to be stable over a long period of time. This prevents tilting movements and, in addition, loosening of the screw, as a result of bone absorption in the region of the thread. This improves, in particular, the fixing of bone fragments.

The invention permits pronounced axial inclination of the screw with respect to the normal to the plate, as a result of which it is possible to fix oblique and sagittal fractures and bone fragments as well as convex and concave bone surfaces.

According to the preferred embodiment of the invention, the screw hole is conical. A further preferred embodiment of the invention provides that the rounded, in particular, spherical, screw head is rounded over sufficient width in the equator region to ensure full wedging in every angled position.

According to a further embodiment, the rounded, in particular spherical, screw head and the conical screw hole are configured such that contact is always between the conical surface and screw head in every possible relative angular position of the screw and plate. Thus, when the screw is positioned obliquely to the maximum permissible extent with respect to the plate, the entire contact surface between the screw head and the hole wall is formed by a rounded section of the screw head and not by an isolated edge section of the screw head as was possible in the prior art. This ensures optimum contact over a wide surface area as well as wedging between the screw head and the plate, which has turned out to be advantageous for the purpose of avoiding loosening as a result of micro movements.

A further embodiment of the invention provides that the screw head is roughened at least at the point at which it comes into contact with the wall of the screw hole. The roughening is such that the friction, in particular the static friction, between the screw head and the screw wall is increased. It is also possible to prepare the wall of the screw hole in a corresponding roughened manner.

The conical screw hole is preferably configured such that the cone angle is between 3° and 5.5°, particularly preferably between 3.5° and 4.5°.

The idea of the invention may also be formulated such that the maximum diameter $D_m$ of the convex, in particular spherical, screw head is larger than ½ $(D_u+D_o)$, where $D_u$ and $D_o$ are the diameters of the screw hole at the bottom plate face and the top plate face, respectively.

A particularly preferred embodiment of the invention provides that, when the screw is located perpendicularly with respect to the plate, the distance $d_c$ of the contact ring from the bottom face of the plate is in the range from 0.6 to 0.8 of the plate thickness ($d_p$).

Another embodiment of the invention provides that, when screwed-in, the screw head is countersunk in the screw hole, i.e., entirely below the top surface.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
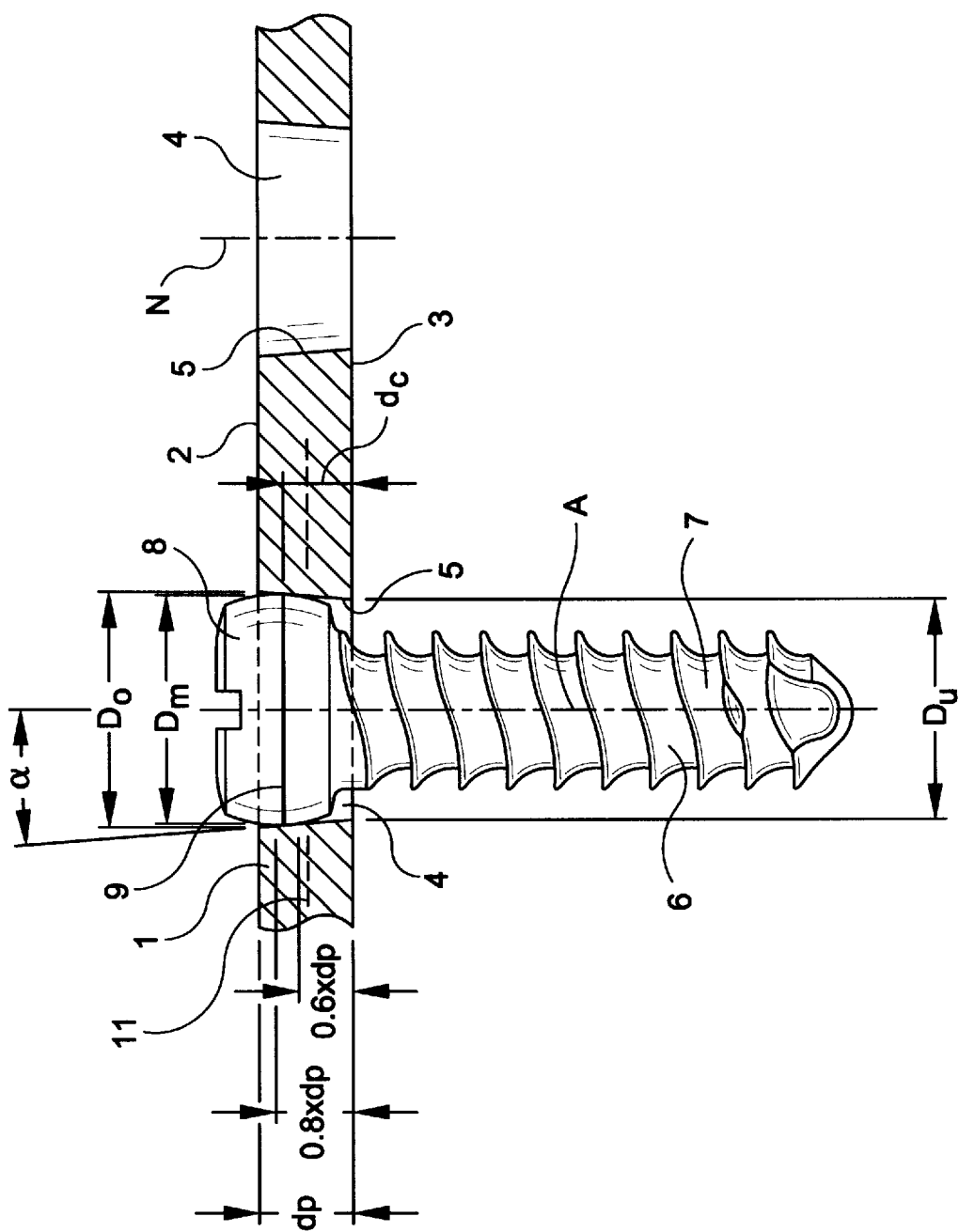
FIG. 1 shows, schematically in section, a first embodiment of an osteosynthesis plate and screw.

The figures show a plate 1 whose dimensions (thickness, etc.) correspond more or less to those of conventional osteosynthesis devices (cf. the prior art cited above). Plate 1 has a top face 2 and a bottom face 3 which, in use, is directed towards the bone. The distance between the top and bottom faces is $d_p$.

A plurality of screw holes 4 extend through the plate 1 from top face 2 to bottom face 3. The diameter $D_o$ of screw holes 4 at top face 2 is larger than the diameter $D_u$ at bottom face 3 of the plate. In this exemplary embodiment, the wall 5 of each screw hole 4 forms the surface of a cone with a preferred cone angle α of 4°.

In use, screws 6 with a screw thread 7 are passed through holes 4 with the screw head 8 being formed spherically, e.g., as a section of a ball. The screw is screwed into the bone in a known manner. In the embodiment shown in FIG. 3, screw head 8 is essentially countersunk in screw hole 4, i.e., when the longitudinal axis A of screw 6 is arranged perpendicularly with respect to the main plane of plate 1 and parallel to the axis of screw hole 4, the end face 8a of screw head 8 forms an essentially continuous plane with top face 2 of the plate 1, i.e., end face 8a of screw head 8 is in alignment with face 2 of plate 1.

When screws 6 are screwed firmly into the bone, they are clamped firmly to wall 5 of holes 4 by means of the wedging action of their screw heads 8. Spherical screw head 8 and wall 5 of the hole are in contact with one another at an annular contact surface 9.

Figure 2:
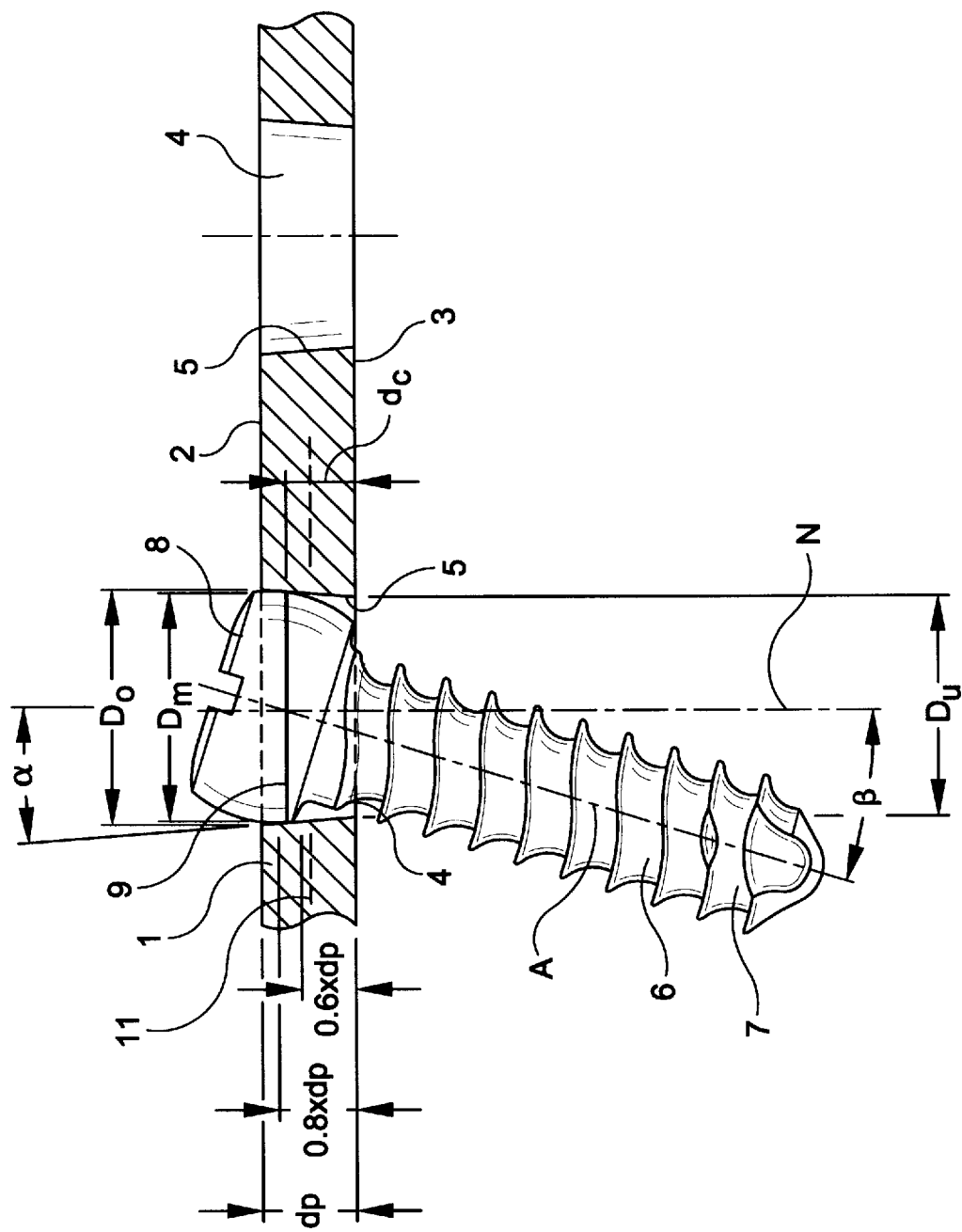
FIG. 2 shows the exemplary embodiment according to FIG. 1 with the screw positioned obliquely.

The maximum diameter $D_m$ of screw head 8 is larger than ½ ($D_o+D_u$), with the result that all points of the approximately circular contact surface 9 are arranged in the top half of the plate whenever screw 8 shown in FIG. 1 is mounted vertically, i.e., when the longitudinal axis A of the screw runs parallel to the normal N to the plate 1. As shown in FIG. 2 in the preferred embodiment, the spherical geometry of screw head 8 is such that, even when screw 6 is positioned obliquely with respect to plate 1, all points of contact surface 9 are essentially located above the center line 11 of plate 1.

Figure 3:
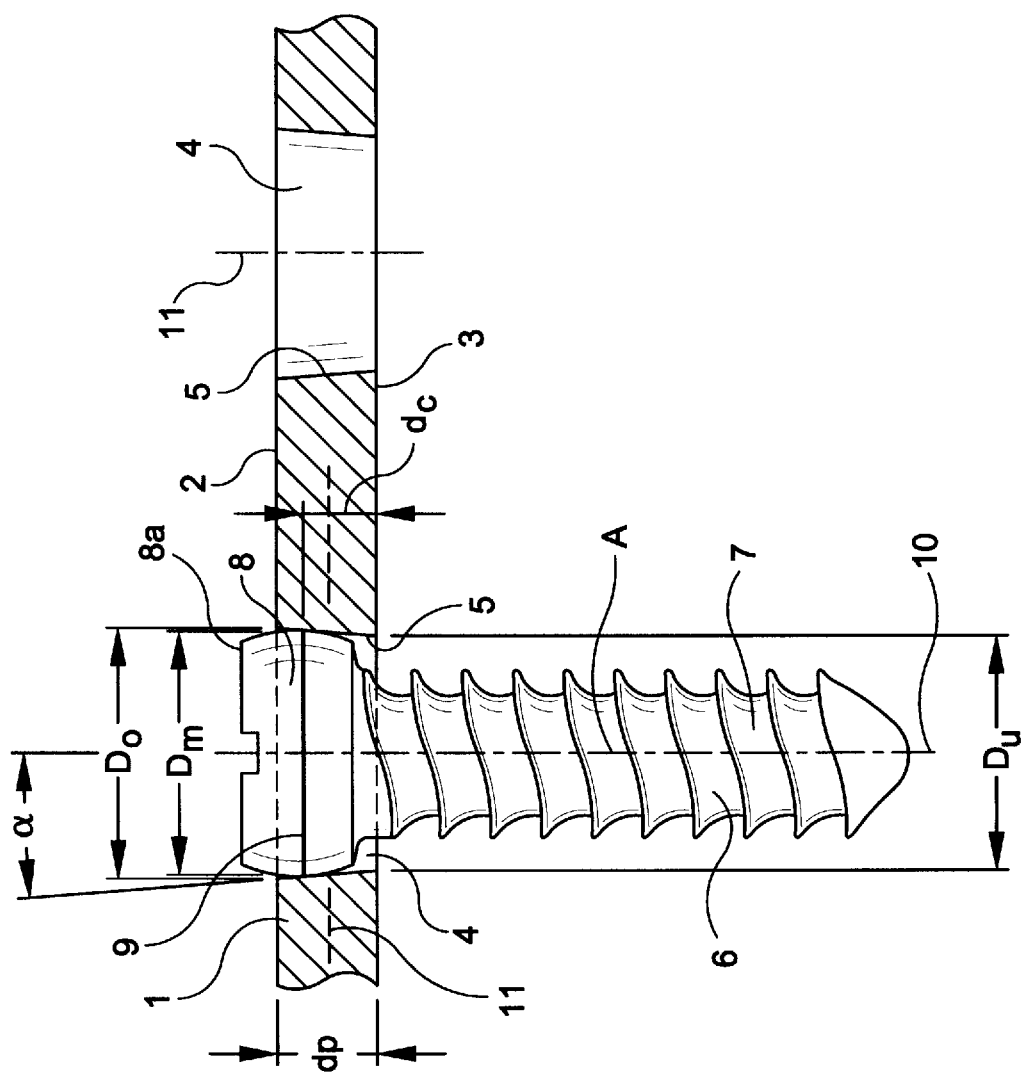
FIG. 3 shows a further embodiment of an osteosynthesis plate and screw.

In the embodiment shown in FIGS. 1 to 3, the distance $d_c$ of contact surface 9 from bottom face 3 of the plate is between 0.6 $d_p$ and 0.8 $d_p$, to be precise, as FIGS. 1 and 2 show, preferably for all possible angular positions of screw 6 with respect to plate 1.

The figures also show the conical shape of screw holes 4 with the cone angle α, which, in the preferred embodiments, is between 3° and 5.5°, particularly between 3.5° and 4.5°, with 4.0° being the preferred choice.

FIG. 2 shows screw 6 with the maximum possible angle of inclination β between the screw axis A and the normal N to the plate 1. This maximum angle of inclination is defined by the screw shaft hitting against the bottom edge of the hole. In most cases, β is no more than about 45° and more commonly no more than 30°.

The illustrated design of the osteosynthesis device ensures that the screws cannot slip through the holes 4 even when subjected to extreme tensile forces and even at their maximum angle with respect to the plate.

The screw head 8 may be roughened at least in the areas in which it contacts wall 5 of the hole. The rough surface may be obtained, for example, by allowing this region of the screw head to remain untreated following the production of the screw such as by the usual anodizing or electrochemical polishing, thus maintaining a certain degree of roughness. The roughness may also be produced specifically, in particular by sand blasting, knurling or other measures. Accordingly, in this embodiment, the roughened surfaces are also not anodized or electrochemically polished.

The tightened screw provides an annular contact surface with the walls which is located entirely in the spherical region of the screw head. This is the case in all possible permissible relative positions between the screw and the plate (see the extreme position shown in FIG. 2). This results in a particularly firm connection, the effect of which can be compared with a weld between the head and the plate.

While several examples of the present invention have been described, it is obvious that many changes and modifications may be made thereunto, without departing from the spirit and scope of the invention.

I claim:

1. An osteosynthesis device comprising:
   a plate with a top face and a bottom face located opposite said top face and directed towards a bone, said plate having a plurality of conical screw holes each of which has a diameter ($D_o$) at the top face of the plate which is larger than a coaxial diameter ($D_u$) at the bottom plate face thus forming a tapered wall therebetween; and
   a plurality of screws which can be screwed into the bone through said screw holes, each screw having an at least a partially spherical rounded head which rests against said screw hole wall along an annular contact surface, wherein when the axis of the screw is aligned with the axis of said hole, said contact surface is closer to the top face of the plate than to the bottom face thereof.

2. The osteosynthesis device according to claim 1 wherein the rounding of the screw head extends in the direction of the screw axis so that with inclination (β) of the screw with respect to the normal (N) to the plate, there is still an annular contact surface between the screw head and the wall of the screw hole.

3. The osteosynthesis device according to claim 1 wherein at least one of the screw head and the wall of the screw hole has a rough surface at least in their region of contact.

4. The osteosynthesis device as set forth in claim 1 wherein the tapered wall is conical with a cone angle (α) in the range from 3° to 5.5°.

5. The osteosynthesis device as set forth in claim 4 wherein the cone angle ($\alpha$) is in the range from 3.5° to 4.5°.

6. The osteosynthesis device as set forth in claim 1 wherein said rounded screw head has a maximum diameter ($D_m$) which is larger than ½ ($D_u+D_o$).

7. The osteosynthesis device as set forth in claim 1 wherein when the screw is located perpendicularly with respect to the face of the plate, a distance ($d_c$) of said contact surface from the bottom face of the plate is in the range of 0.6 to 0.8 of the plate thickness ($D_P$) at said hole.

8. The osteosynthesis device according to claim 7 wherein the screw head is countersunk in the screw hole when fully screwed in.

9. The osteosynthesis device as set forth in claim 1 wherein when the screw is located at an angle with respect to the plate, all points of the contact surface are closer to the top face of the plate than to the bottom face thereof.

10. An osteosynthesis device comprising:

a plate having a top face, a bottom face and a plurality of screw holes therein, said screw holes being in the form of a cone tapering from a larger diameter at said top face to a smaller diameter at said bottom face; and a screw having at least a part spherical head with a diameter greater than a diameter of said cone at a midpoint between said top and bottom faces of said plate.

11. The osteosynthesis device as set forth in claim 10 wherein said screw head diameter is such that a contact surface is formed between the screw head and a wall of said conical hole which surface is located towards said top face of said plate from said diameter at said midpoint of said cone when said screw is angled with respect to a central axis of said cone.

12. The osteosynthesis device as set forth in claim 11 wherein at least when the screw is located perpendicularly with respect to the face of the plate, a distance ($d_c$) of said contact surface from the bottom face of the plate is in the range of 0.6 to 0.8 of the plate thickness ($d_p$) at said hole.

* * * * *